United States Patent
Scheibel et al.

(10) Patent No.: US 7,538,080 B2
(45) Date of Patent: *May 26, 2009

(54) MODIFIED ALKOXYLATED POLYOL COMPOUNDS

(75) Inventors: Jeffrey John Scheibel, Loveland, OH (US); Julie Ann Menkhaus, Cleves, OH (US); Xinbei Song, Cincinnati, OH (US); Eva Schneiderman, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/903,574

(22) Filed: Sep. 24, 2007

(65) Prior Publication Data

US 2008/0015398 A1  Jan. 17, 2008

Related U.S. Application Data

(62) Division of application No. 11/015,574, filed on Dec. 17, 2004.

(60) Provisional application No. 60/531,385, filed on Dec. 19, 2003.

(51) Int. Cl.
| | |
|---|---|
| *C11D 11/04* | (2006.01) |
| *C11D 1/02* | (2006.01) |
| *C11D 3/37* | (2006.01) |
| *C07C 211/02* | (2006.01) |
| *C07C 213/02* | (2006.01) |

(52) U.S. Cl. .............. 510/475; 510/350; 510/351; 510/360; 510/413; 510/421; 510/423; 510/426; 510/499; 510/524; 564/469; 564/475; 564/478

(58) Field of Classification Search ............. 510/350, 510/351, 360, 413, 421, 423, 426, 475, 499, 510/524; 564/469, 475, 478

See application file for complete search history.

(56) References Cited

U.S. PATENT DOCUMENTS

| | | | | |
|---|---|---|---|---|
| 4,927,961 | A | * | 5/1990 | Fock et al. ............ 562/103 |
| 4,990,269 | A | * | 2/1991 | Andreasson et al. ...... 507/246 |
| 5,371,119 | A | | 12/1994 | Bohlander et al. |
| 5,672,761 | A | * | 9/1997 | Adkins et al. ............. 564/475 |
| 2002/0142929 | A1 | | 10/2002 | Smith et al. |
| 2005/0153867 | A1 | | 7/2005 | Scheibel et al. |

FOREIGN PATENT DOCUMENTS

| | | |
|---|---|---|
| EP | 0 288067 | 10/1988 |
| EP | 0325054 | 7/1989 |
| JP | 10-081744 | 3/1998 |
| JP | 10-140182 | 5/1998 |
| WO | WO 01/98388 | 12/2001 |

* cited by examiner

*Primary Examiner*—Brian P Mruk
(74) *Attorney, Agent, or Firm*—Stephen T. Murphy; Jerry J. Yetter; Kim W. Zerby

(57) ABSTRACT

A modified polyol compound having alkoxylation and having at least one anionic capping unit, uses of the modified polyol compound having alkoxylation and having at least one anionic capping unit and cleaning compositions comprising the same.

2 Claims, No Drawings

US 7,538,080 B2

MODIFIED ALKOXYLATED POLYOL COMPOUNDS

CROSS REFERENCE TO RELATED APPLICATION

This application is a Divisional Application of U.S. application Ser. No. 11/015,574, filed Dec. 17, 2004, which claims the benefit under 35 U.S.C. § 119(e) of U.S. provisional application No. 60/531,385, filed Dec. 19, 2003.

FIELD OF THE INVENTION

This invention relates to modified alkoxylated polyol compounds, methods of making modified alkoxylated polyol compounds, and cleaning compositions comprising the same.

BACKGROUND OF THE INVENTION

Polyol compounds such as sugars like sucrose or maltitose are known as a sustainable and readily available raw material. Ethoxyates of maltitol is known, e.g., CAS 503446-80-8. This material has been widely disclosed as a surfactant for cosmetic and other personal care applications such as that discussed in JP 2003-096182. Other known ethoxylated polyols include: ethoxylated manitol (CAS 53047-01-2), ethoxylated inostol (CAS 503446-79-5), ethoxylated sorbitol (CAS 53694-15-8). JP 10-081744 discusses the production of polyetherpolyols by adding alkylene oxides to saccharide in the presence of amine catalysts. However, as "catalyst" implies, the amine catalysts do not become incorporated into the polyetherpolyol structure.

Also known are a series of amine terminated ethoxylates known in the trade as JEFFAMINES® sold by Huntsman. These are mainly derived from polyethylene glycol and mixtures of polyethylene glycol and polypropylene glycol where the glycols are aminated directly with ammonia and a catalyst. These are called JEFFAMINE D® and JEFFAMINE ED® series. The most complex mixture of the JEFFAMINES® series is the T series. The JEFFAMINES® are based on either trimethylolpropane or glycerine and thus have three ammonia terminated ethoxy/propoxy branches radiating from the glycerin or trimethylolpropane core.

Amination of polyols with ammonia and other amines is further exemplified in U.S. Pat. No. 5,371,119, but uses modification of the polyol specifically via epichlorohydrin to form a polyol bis-halohydrin followed by reaction with ammonia or an amine to form repeating networks of amino polyols. This results in formation of a complex polymerized mixture containing multiple polyols linked randomly via the reactive halo hydrin. This complex mixture is not believed to be of value to formulators of cleaning compositions for the purpose of providing cleaning benefits and is targeted towards forming emulsifiers.

Simple amination of polyols are described in WO 01/98388 A1 discussing simple aminated polyols, further reacted with aldehydes, in particular formaldehyde, to make complex polymeric networks. Included in these complex structures is the ability to have sulfide, carboxylate, alkyl esters, alkyl sulphonates, and alkyl phosphates as a functional unit of the complex structure. However, the resulting complex polymeric networks is not believed to be of value to formulators of cleaning compositions for the purpose of providing cleaning benefits. Additionally, it has not been taught to manipulate these materials in a controlled and specific manner. Selective modification of sugar derived polyols to provide modified polyols where the star like structure is tuned to meet the needs of detergent formulators is highly desirable.

There also exists a need for materials that are relatively easy to manufacture from sustainable and readily available raw materials, which may be broadly tuned to address specific performance requirements.

Stressed conditions also give the additional problem of having anionic surfactants such as linear alkylbenzene sulfonates or alkyl sulfates form larger order aggregates. The aggregation of the anionic surfactant reduces the amount of the anionic surfactant available to clean.

There exists a need for materials that are relatively easy to manufacture from sustainable and readily available raw materials, which may be tuned in a controlled and specific manner to address specific formulability and performance requirements. A multifunctional material that provides cleaning and gives increased surfactant availability by preventing formation of larger ordered aggregates of anionic surfactant with free hardness during use is desired.

Specific performance requirements include providing cleaning of hydrophobic stains (grease, oil) to hydrophilic stains (clay) associated with outdoor soils. Other performance requirements include used in personal care compositions, such as contact lens solution, uses in adhesives, vulcanization of rubbers, use in polyurethane processes, use as dye additives, use as a dispersant in agricultural applications, use as dispersants for inks, asphalt dispersants, surfactant dissolution aides, in use surfactant solubilizers in presence of calcium and magnesium among other performance requirements.

Formulability of some of the current commercial polymers, which provide cleaning of outdoor soils, into granular and liquid laundry detergents, hard surface cleaners, dish cleaning compositions, personal care compositions as well as oil drilling compositions continues to challenge detergent formulators.

SUMMARY OF THE INVENTION

The present invention relates to compounds, processes, cleaning compositions, and methods of using said compounds and compositions characterized by comprising a polyol compound, the polyol compound comprising at least three hydroxy moieties, at least one of the hydroxy moieties further comprising a alkoxy moiety, the alkoxy moiety is selected from the group consisting of ethoxy, propoxy, butoxy and mixtures thereof; further wherein at least one of the hydroxy moieties further comprise an anionic capping unit.

The present invention further relates compounds, processes, cleaning compositions, and methods of using said compounds and compositions characterized by comprising a polyol compound, the polyol compound comprising at least three hydroxy moieties, at least one of the hydroxy moieties further comprising a alkoxy moiety, the alkoxy moiety is selected from the group consisting of ethoxy, propoxy, butoxy and mixtures thereof; further wherein at least one of the hydroxy moieties is replaced by and thus further comprises an anionic capping unit and at least one of the hydroxy moieties is substituted by an amine capping unit.

The present invention further relates compounds, processes, cleaning compositions, and methods of using said compounds and compositions characterized by comprising a polyol compound, the polyol compound comprising at least three hydroxy moieties, at least one of the hydroxy moieties further comprising a alkoxy moiety, the alkoxy moiety is selected from the group consisting of ethoxy, propoxy, butoxy and mixtures thereof; further wherein at least one of the hydroxy moieties is replaced by and thus further comprises an anionic capping unit and at least one of the hydroxy moieties is substituted by a quaternary amine capping unit.

The present invention further relates compounds, processes, cleaning compositions, and methods of using said compounds and compositions characterized by comprising a polyol compound, the polyol compound comprising at least three hydroxy moieties, at least one of the hydroxy moieties further comprising a alkoxy moiety, the alkoxy moiety is selected from the group consisting of ethoxy, propoxy, butoxy and mixtures thereof; further wherein at least one of the hydroxy moieties is replaced by and thus further comprises an anionic capping unit, at least one of the hydroxy moieties is substituted by an amine capping unit and at least one of the hydroxy moieties is substituted by a quaternary amine capping unit.

DETAILED DESCRIPTION OF THE INVENTION

There exists a need for materials that are relatively easy to manufacture from sustainable and readily available raw materials, which may be broadly tuned to address specific formulability and performance requirements.

Polyol compounds such as sugar based materials and polyethylene/polypropylene glycol materials are sustainable and readily available raw materials that lend themselves to be broadly tuned to address specific formulability and performance requirements. As used herein "tune" means having the ability to manipulate the chemical structure of the polyol compounds to achieve distinguishing chemical functionality. For example, an alkoxylated polyol compound modified by comprising an anionic capping unit is a tuned structure giving desired characteristics for specific formulability and performance requirements. Another example, an alkoxylated polyol compound modified by comprising an anionic capping unit and amine capping unit is a tuned structure giving desired characteristics. Another example is when an alkoxylated polyol compound is modified by comprising an anionic capping unit and a quaternary amine capping unit, is a tuned structure giving desired characteristics. Finally another example may contain both elements of the two examples, thus containing an anionic capping unit and an amine and quaternary amine capping unit.

The polyol compounds useful in the present invention comprises at least three hydroxy moieties, preferably more than three hydroxy moieties. Most preferably six or more hydroxy moieties. At least one of the hydroxy moieties further comprising a alkoxy moiety, the alkoxy moiety is selected from the group consisting of ethoxy (EO), propoxy (PO), butoxy (BO) and mixtures thereof preferably ethoxy and propoxy moieties, more preferably ethoxy moieties. The average degree of alkoxylation is from about 1 to about 100, preferably from about 4 to about 60, more preferably from about 10 to about 40. Alkoxylation is preferably block alkoxylation.

The polyol compounds useful in the present invention further have at least one of the alkoxy moieties comprising at least one anionic capping unit. Further modifications or tuning of the compound may occur, but one anionic capping unit must be present in the compound of the present invention. One embodiment comprises more than one hydroxy moiety further comprising an alkoxy moiety having an anionic capping unit. For example formula (I):

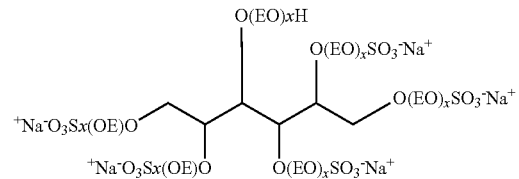

formula (I)

wherein x of formula (I) is from about 1 to about 100, or such as from about 10 to about 40.

Suitable anionic capping unit include sulfate, sulfosuccinate, succinate, maleate, phosphate, phthalate, sulfocarboxylate, sulfodicarboxylate, propanesultone, 1,2-disulfopropanol, sulfopropylamine, sulphonate, monocarboxylate, methylene carboxylate, ethylene carboxylate, carbonates, mellitic, pyromellitic, sulfophenol, sulfocatechol, disulfocatechol, tartrate, citrate, acrylate, methacrylate, poly acrylate, poly acrylate-maleate copolymer, and mixtures thereof. Preferably the anionic capping units are sulfate, sulfosuccinate, succinate, maleate, sulfonate, methylene carboxylate and ethylene carboxylate.

Suitable polyol compounds for starting materials for use in the present invention include maltitol, sucrose, xylitol, glycerol, pentaerythitol, glucose, maltose, matotriose, maltodextrin, maltopentose, maltohexose, isomaltulose, sorbitol, poly vinyl alcohol, partially hydrolyzed polyvinylacetate, xylan reduced maltotriose, reduced maltodextrins, polyethylene glycol, polypropylene glycol, polyglycerol, diglycerol ether and mixtures thereof. Good examples include the polyol compound being selected as sorbitol, maltitol, sucrose, xylan, polyethylene glycol, polypropylene glycol and mixtures thereof. Another group for the polyol compound is sorbitol, maltitol, sucrose, xylan, and mixtures thereof.

Tuning of the polyol compounds can be derived from one or more modifications, dependant upon the desired formulability and performance requirements. Tuning requires anionic modifications and can include incorporating a cationic or zwitterionic charge modifications to the polyol compounds.

In one embodiment of the present invention, at least one hydroxy moiety comprises an alkoxy moiety, wherein the alkoxy moiety further comprises at least one anionic capping unit.

In another embodiment of the present invention, at least one hydroxy moiety comprises an alkoxy moiety, wherein the alkoxy moiety further comprises more than one anionic capping unit, wherein at least one anionic capping unit, but less than all anionic capping units, is then selectively substituted by a amine capping unit. The amine capping unit is selected from a primary amine containing capping unit, a secondary amine containing capping unit, a tertiary amine containing capping unit, and mixtures thereof.

Suitable primary amines for the primary amine containing capping unit include monoamines, diamine, triamine, polyamines, and mixtures thereof. Suitable secondary amines for the secondary amine containing capping unit include monoamines, diamine, triamine, polyamines, and mixtures thereof. Suitable tertiary amines for the tertiary amine containing capping unit include monoamines, diamine, triamine, polyamines, and mixtures thereof.

Suitable monoamines, diamines, triamines or polyamines for use in the present invention include ammonia, methyl amine, dimethylamine, ethylene diamine, dimethylaminopropylamine, bis dimethylaminopropylamine (bis DMAPA), hexemethylene diamine, benzylamine, isoquinoline, ethylamine, diethylamine, dodecylamine, tallow triethylenediamine, mono substituted monoamine, monosubstituted diamine, monosubstituted polyamine, disubstituted monoamine, disubstiuted diamine, disubstituted polyamine, trisubstituted triamine, tri-substituted polyamine, multisubstituted polyamine comprising more than three substitutions provided at least one nitrogen contains a hydrogen, and mixtures thereof.

In another embodiment of the present invention, at least one of nitrogens in the amine capping unit is quaternized. As used herein "quaternized" means that the amine capping unit is given a positive charge through quaternization or protonization of the amine capping unit. For example, bis-DMAPA contains three nitrogens, only one of the nitrogens need be quaternized. However, it is preferred to have all nitrogens quaternized on any given amine capping unit.

The tuning or modification may be combined depending upon the desired formulability and performance requirements. Non-limiting examples of modified polyol compounds of the present invention include:

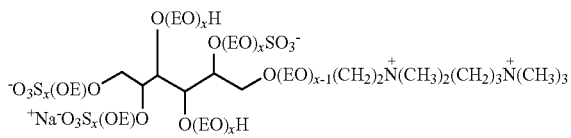

formula (II) wherein x of formula (I) is from about 1 to about 100; and such as from about 10 to about 40.

such as from about 10 to about 40; to form an alkoxylated polyol comprising at least one alkoxy moiety. Alternatively, an alkoxylated polyol, such as CAS 52625-13-5, a propoxylated sorbitol or sorbitol polyoxy ethylene ether available from Lipo Chemicals Inc., may be used as the starting material of the present invention. If the average degree of alkoxylation is not a desired level, an alkoxylation step may be used to achieve the desired degree of alkoxylation from about 1 to about 100, and such as from about 4 to about 60; further such as from about 10 to about 40. Next, the process comprises the step of reacting at least one alkoxy moiety of the compound with an anionic capping unit to form an anionic alkoxylated polyol, although more anionic capping units may be selected.

In one embodiment the process comprises another step of substituting at least one anionic capping unit of the anionic alkoxylated polyol with an amine capping unit to form an anionic aminated alkoxylated polyol. In this process only certain anionic capping units may be substituted such as sulfate, phosphate and carbonate. The process may further comprise the step of quaternizing at least one of the nitrogens in the amine capping of the anionic aminated alkoxylated polyol to form a zwitterionic alkoxylated polyol. Quaternization can be performed on any of the anionic aminated alkoxylated polyols. In one embodiment, the process comprises the step of alkoxylating some or most of the hydroxy moieties of the polyol such that the degree of alkoxylation is from about 1 to about 100; and such as from about 4 to about 60, further such as from about 10 to about 40; to form an alkoxylated polyol. The process further comprises the step of reacting the alkoxy moiety of the alkoxylated polyol with at least one

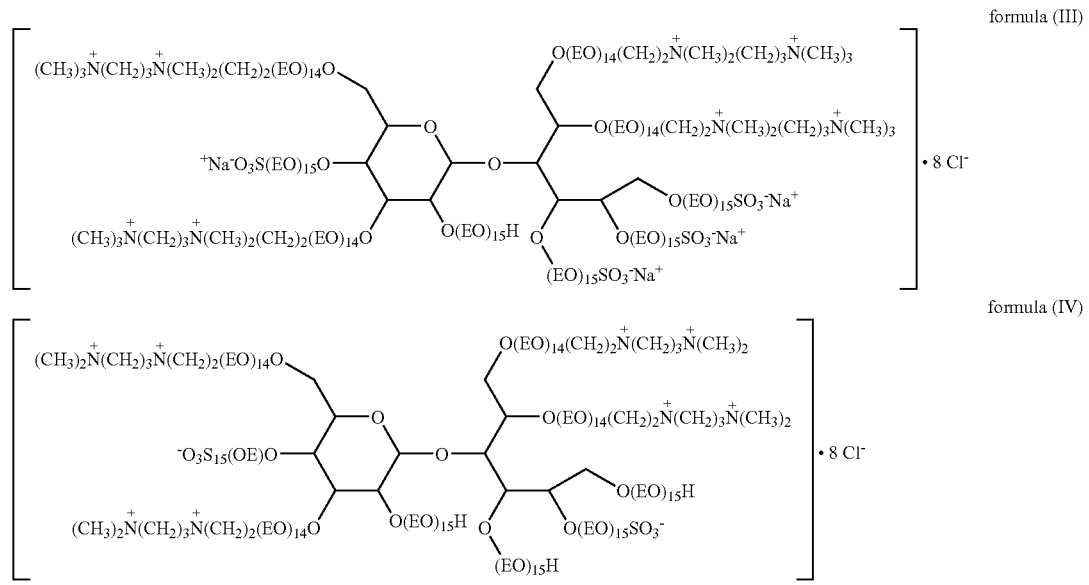

Process of Making

The present invention also relates to a process for making the compound of the present invention. The process for making the compound of the present invention comprises the optional step of alkoxylating a polyol compound comprising at least three hydroxy moieties such that the average degree of alkoxylation of at least one hydroxy moiety is between about 1 and about 100; and such as from about 4 to about 60; further anionic capping unit containing as least one of the following anionic groups; sulfate, phosphate and carbonate; to form an anionic alkoxylated polyol. The process may partially or completely react the alkoxy moiety of the alkoxylated polyol with an anionic capping unit. It is also understood that anionic capping units other than sulfate, phosphate or carbonate may also be present in the anionic alkoxylated polyol. Preferably all alkoxy moieties comprise an anionic capping unit.

Optionally, the process comprises the step of substituting the anionic capping unit with an amine capping unit selected from sulfate, phosphate and carbonate and mixtures thereof, to form an aminated anionic alkoxylated polyol (scheme I below). The substitution of the anionic capping units present with an amine capping unit may be partial or complete. Preferably the subsitution of the anionic capping unit with the amine capping unit is partial forming an anionic aminated alkoxylated polyol.

Optionally, the process also comprises the process of providing an aminated alkoxylated polyol by direct amination of the alkoxylated polyol using catalytic amination (scheme II below)

Optionally, the process may further comprise the step of quaternizing at least one of the nitrogens of the amine capping unit of the anionic aminated alkoxylated polyol forming a zwitterionic alkoxylated polyol. The quaternization of the amine capping unit of the anionic aminated alkoxylated polyol may be partial or complete. In one embodiment, the quaternization is partial. In another embodiment, the quaternization is complete. The quaternization of the nitrogens of the amine capping unit may be partial or complete, preferably complete. A nonlimiting synthesis scheme is exemplified in Synthesis Scheme I and Synthesis Scheme II below:

Synthesis Scheme I Anionic aminated alkoxylated polyol

STEP 1

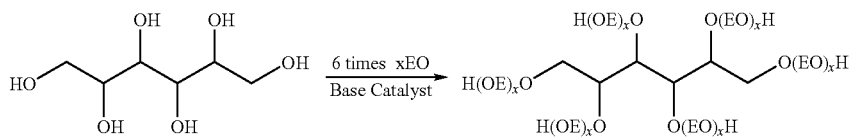

STEP 2

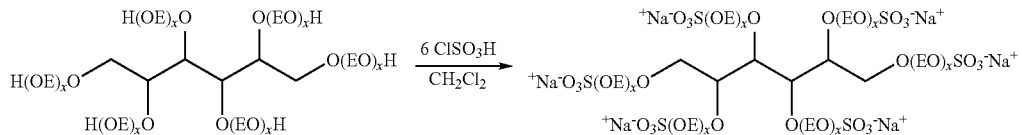

STEP 3

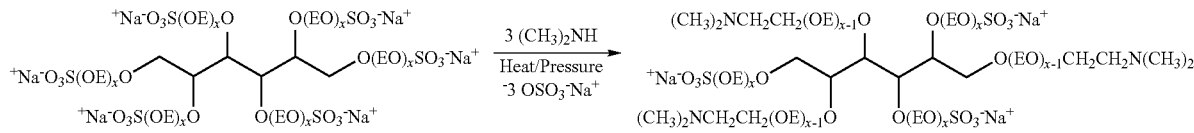

STEP 4

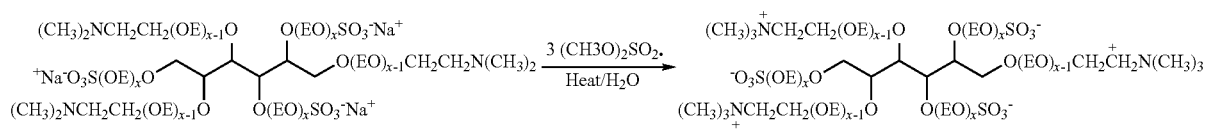

The process may comprise optionally Step 1, Step 2, and optionally, Step 3 and 4. The step to providing the anionic aminated alkoxylated polyol via a neucleophilic substitution of sulfate moieties by an amine capping unit should be noted. This is a nonlimiting example as phosphate or carbonate groups may also be used for substitution by an amine capping unit.

Synthesis Scheme II:

STEP 1

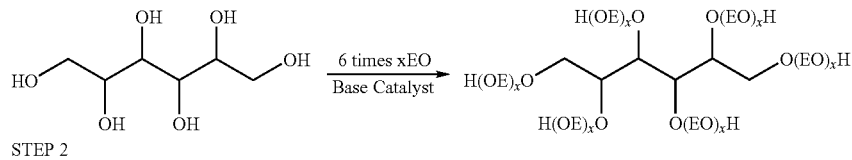

STEP 2

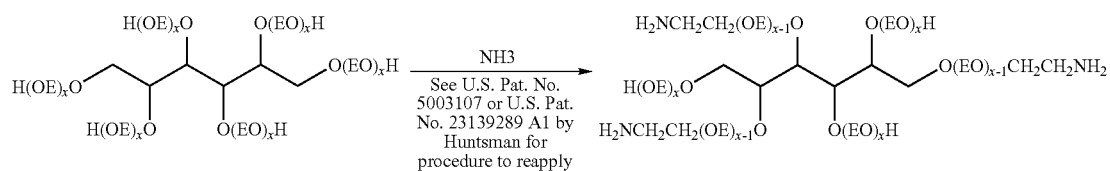

STEP 3

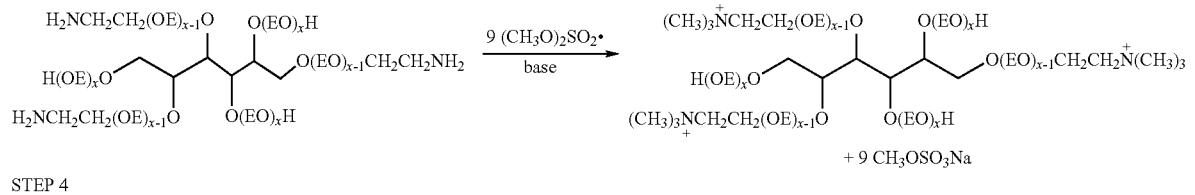

STEP 4

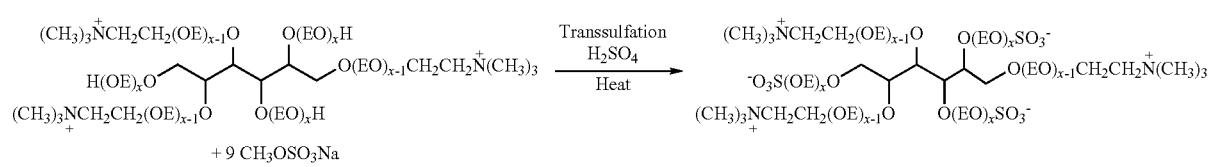

Scheme II is distinguished from Scheme I in two areas; (1) direct substitution of the terminal hydroxy moieties is accomplished by catalytic oxidation/reduction using metal catalysts and hydrogen; (2) sulfation is carried out after amination and quaternization by transulfation as disclosed in U.S. Pat. No. 6,452,035. A zwitterionic alkoxylated polyol of the same composition may be prepared by either Scheme I or Scheme II above. One of skill in the art will recognized that other amine capping units may be used, including but not limited to ammonia or dimethylaminopropylamine.

A specific description of the process of the present invention is described in more detail below.

Ethoxylation of Polyol

Ethoxylation of the polyol, such as sorbitol, may be completed by any known technique, such as that described in EP 174436 A1 Propoxylation and butoxylation may also be completed by known techniques.

Add sorbitol (17.5 g, 0.0962 mol) to an autoclave, purge the autoclave with nitrogen, heat sorbitol to 110-120° C.; autoclave stirred and apply vacuum to about 20 mmHg.

Vacuum is continuously applied while the autoclave is cooled to about 110-120° C. while introducing 6.2 g of a 25% sodium methoxide in methanol solution (0.0288 moles, to achieve a 5% catalyst loading based upon hydroxy moieties).

The methanol from the methoxide solution is removed from the autoclave under vacuum. A device is used to monitor the power consumed by the agitator. The agitator power is monitored along with the temperature and pressure. Agitator power and temperature values gradually increase as methanol is removed from the autoclave and the viscosity of the mixture increases and stabilizes in about 1.5 hours indicating that most of the methanol has been removed. The mixture is further heated and agitated under vacuum for an additional 30 minutes.

Vacuum is removed and the autoclave is cooled to or kept at 110° C. while it is being charged with nitrogen to 1725 kPa (250 psia) and then vented to ambient pressure. The autoclave is charged to 1380 kPa (200 psia) with nitrogen. Ethylene oxide is added to the autoclave incrementally while closely monitoring the autoclave pressure, temperature, and ethylene oxide flow rate while maintaining the temperature between 110 and 120° C. and limiting any temperature increases due to reaction exotherm. After the addition of 483 g of ethylene oxide (10.97 mol, resulting in a total of 19 moles of ethylene oxide per mol of OH), the temperature is increased to 120° C. and the mixture stirred for an additional 2 hours.

The reaction mixture is then collected into a 22 L three neck round bottomed flask purged with nitrogen. The strong alkali catalyst is neutralized by slow addition of 2.8 g methanesulfonic acid (0.00288 moles) with heating (110° C.) and mechanical stirring. The reaction mixture is then purged of residual ethylene oxide and deodorized by sparging an inert gas (argon or nitrogen) into the mixture through a gas dispersion frit while agitating and heating the mixture to 120° C. for 1 hour. The final reaction product, approximately 500 g, is cooled slightly, and poured into a glass container purged with nitrogen for storage.

Alternatively, polyol may be purchased with a degree of alkoxylation that is at or below that desired, such as CAS 52625-13-5, a propoxylated sorbitol or sorbitol polyoxy ethylene ether available from Lipo Chemicals Inc. Wherein the desired degree of alkoxylation is achieved by the processes known and/or described above.

Sulfation of Sorbitol $EO_{114}$ (Average of 19 EO Moieties Per Hydroxy Moiety)

Weigh into a 500 ml Erlenmeyer flask Sorbitol $E_{114}$ (299.7 g, 0.058 mol) and methylene chloride (300 g) ("the solution")_. Equip the flask with a magnetic stirring bar and stir until complete dissolution. Place the flask in an ice bath until the solution reaches about 10° C. Stir vigorous while slowing pouring chlorosulfonic acid (48.3 g, 0.415 mol) over the period of about 5 minutes to form a reaction solution. Stir the reaction solution in the ice bath for 1.5 hours.

Place a solution of sodium methoxide (197 g of 25% in methanol) in 50 g of methylene chloride in a lL Erlenmeyer flask ("base solution") and chill in an ice bath until the temperature of the solution reaches about 10° C. Stir the base solution vigorous using a magnetic stirring bar. Slowly pour the reaction solution into the base solution over a period of about 3 minutes. A mild exotherm should be observed. The resulting solution becomes milky as salts form. After addition is complete, measure the pH to be about 12. Add to this resulting solution about 100 ml of distilled water, and transfer the resulting emulsion to a 1 L round bottom flask and use a rotary evaporator at 50° C. to strip, in portions, to obtain a clear solution. Transfer the clear solution to a Kulgelrohr apparatus. At 60° C. and 133 Pa (1 mm Hg) strip the solution to yield 366 g of off-white waxy solid, 90% active (10% salts).

Carbon NMR spectrum (500 MHz; pulse sequence: s2pul, solvent $D_2O$; relax. delay 0.300 sec, pulse 45.0; acq. time 1.090 sec) shows an absence of alcohol groups at about 60 ppm and the emergence of a new peak at about 67 ppm consistent with formation of the end group sulfate. Proton NMR spectrum (500 MHz or 300 MHz; pulse sequence: s2pul, solvent $D_2O$; relax. delay 1.000 sec, pulse 45.0; acq. time 2.345 sec) shows a new peak at about 4 ppm which was integrated against the ethoxy group protons at about 3.5 ppm and is consistent with the molecule having 6 end group sulfates.

EXAMPLE 2

Amination of Sorbitol $EO_{114}$ Hexasulfate of Example 1

Weigh into a 200 ml glass liner sorbitol $EO_{114}$ hexasulfate (61.3 g of 90% active, 0.0095 mol) and 3-(dimethylamino) propylamine ("DMAPA" 18.5 g, 0.181 mol). Heat the liner in a rocking autoclave at 152 kPa (150 psig) under nitrogen until the temperature reaches 165° C. and hold at 165° C. for 2 hours. Cool to room temperature (20-25° C.). Take the material up in 150 ml of methylene chloride and centrifuge to separate the salts. Transfer the supernatant to a 500 ml round bottom flask and strip the supernatant on a rotary evaporator at 50° C. until most (less than 5 mL) of the solvent is removed. Heat on a Kugelrohr apparatus at 120° C. and 133 Pa (1 mm Hg) for 30 minutes to remove excess amine to afford 47.8 g of brown hard solid. Proton NMR (500 MHz or 300 MHz; pulse sequence: s2pul, solvent $D_2O$; relax. delay 0.300 sec, pulse 45.0; acq. time 3.744 sec) indicated about 3 sulfates and about 2 DMAPA per molecule.

EXAMPLE 3

Quaternization of Amine Containing Sulfate of Example 2

Dissolve an aminated Sorbitol $EO_{114}$ in 100 g of methylene chloride in a 500 ml round bottom flask equipped with a magnetic stirring bar and chill in an ice bath until the temperature reaches 10° C. Adjust the solution to a pH 12 with sodium methoxide (25% solution in methanol). Add to the solution methyl iodide (15.0 g, 0.106 mol). Stopper the flask and stir the solution overnight (about 14 hours). Strip the solution on a Kugelrohr apparatus at 50° C. and 133 Pa (1 mm Hg) to afford 66 g of tacky brown solid. Proton NMR (500 MHz or 300 MHz; pulse sequence: s2pul, solvent $D_2O$; relax. delay 1.000 sec, pulse 45.0; acq. time 2.345 sec) indicated that all nitrogens in the amine capping unit were fully quaternized.

Cleaning Compositions

The present invention further relates to a cleaning composition comprising the modified alkoxylated polyol compound of the present invention. The cleaning compositions can be in any conventional form, namely, in the form of a liquid, powder, granules, agglomerate, paste, tablet, pouches, bar, gel, types delivered in dual-compartment containers, spray or foam detergents, premoistened wipes (i.e., the cleaning composition in combination with a nonwoven material such as that discussed in U.S. Pat. No. 6,121,165, Mackey, et al.), dry wipes (i.e., the cleaning composition in combination with a nonwoven materials, such as that discussed in U.S. Pat. No. 5,980,931, Fowler, et al.) activated with water by a consumer, and other homogeneous or multiphase consumer cleaning product forms.

In addition to cleaning compositions, the compounds of the present invention may be also suitable for use or incorporation into industrial cleaners (i.e. floor cleaners). Often these cleaning compositions will additionally comprise surfactants and other cleaning adjunct ingredients, discussed in more detail below. In one embodiment, the cleaning composition of the present invention is a liquid or solid laundry detergent composition.

In another embodiment, the cleaning composition of the present invention is a hard surface cleaning composition, preferably wherein the hard surface cleaning composition impregnates a nonwoven substrate. As used herein "impregnate" means that the hard surface cleaning composition is placed in contact with a nonwoven substrate such that at least a portion of the nonwoven substrate is penetrated by the hard surface cleaning composition, preferably the hard surface cleaning composition saturates the nonwoven substrate.

In another embodiment the cleaning composition is a liquid dish cleaning composition, such as liquid hand dishwashing compositions, solid automatic dishwashing cleaning compositions, liquid automatic dishwashing cleaning compositions, and tab/unit does forms of automatic dishwashing cleaning compositions.

The cleaning composition may also be utilized in car care compositions, for cleaning various surfaces such as hard wood, tile, ceramic, plastic, leather, metal, glass. This cleaning composition could be also designed to be used in a personal care composition such as shampoo composition, body wash, liquid or solid soap and other cleaning composition in which surfactant comes into contact with free hardness and in all compositions that require hardness tolerant surfactant system, such as oil drilling compositions.

Modified Alkoxylated Polyol Compounds

The cleaning composition of the present invention may comprise from about 0.005% to about 30%, and such as from about 0.01% to about 10%, further such as from about 0.05% to about 5% by weight of the cleaning composition of a modified polyol compound as described herein.

Surfactants—The cleaning composition of the present invention may comprise a surfactant or surfactant system comprising surfactants selected from nonionic, anionic, cationic, ampholytic, zwitterionic, semi-polar nonionic surfactants; and other adjuncts such as alkyl alcohols, or mixtures thereof. The cleaning composition of the present invention further comprises from about from about 0.01% to about 90%, and such as from about 0.01% to about 80%, further such as from about 0.05% to about 50%, more further such as from about 0.05% to about 40% by weight of the cleaning composition of a surfactant system having one or more surfactants.

Anionic Surfactants

Nonlimiting examples of anionic surfactants useful herein include: $C_8$-$C_{18}$ alkyl benzene sulfonates (LAS); $C_{10}$-$C_{20}$ primary, branched-chain and random alkyl sulfates (AS); $C_{10}$-$C_{18}$ secondary (2,3) alkyl sulfates; $C_{10}$-$C_{18}$ alkyl alkoxy sulfates (AE,S) wherein x is from 1-30; $C_{10}$-$C_{18}$ alkyl alkoxy carboxylates comprising 1-5 ethoxy units; mid-chain branched alkyl sulfates as discussed in U.S. Pat. Nos. 6,020, 303 and 6,060,443; mid-chain branched alkyl alkoxy sulfates as discussed in U.S. Pat. Nos. 6,008,181 and 6,020,303; modified alkylbenzene sulfonate (MLAS) as discussed in WO 99/05243, WO 99/05242 and WO 99/05244; methyl ester sulfonate (MES); and alpha-olefin sulfonate (AOS).

Nonionic Surfactants

Non-limiting examples of nonionic surfactants include: $C_{12}$-$C_{18}$ alkyl ethoxylates, such as, NEODOL® nonionic surfactants from Shell; $C_6$-$C_{12}$ alkyl phenol alkoxylates wherein the alkoxylate units are a mixture of ethyleneoxy and propyleneoxy units; $C_{12}$-$C_{18}$ alcohol and $C_6$-$C_{12}$ alkyl phenol condensates with ethylene oxide/propylene oxide block alkyl polyamine ethoxylates such as PLURONIC® from BASF; $C_{14}$-$C_{22}$ mid-chain branched alcohols, BA, as discussed in U.S. Pat. No. 6,150,322; $C_{14}$-$C_{22}$ mid-chain branched alkyl alkoxylates, BAEX, wherein x 1-30, as discussed in U.S. Pat. Nos. 6,153,577, 6,020,303 and 6,093,856; Alkylpolysaccharides as discussed in U.S. Pat. No. 4,565,647 Llenado, issued Jan. 26, 1986; specifically alkylpolyglycosides as discussed in U.S. Pat. Nos. 4,483,780 and 4,483,779; Polyhydroxy fatty acid amides (GS-base) as discussed in U.S. Pat. No. 5,332, 528; and ether capped poly(oxyalkylated) alcohol surfactants as discussed in U.S. Pat. No. 6,482,994 and WO 01/42408.

Cationic Surfactants

Non-limiting examples of anionic surfactants include: the quaternary ammonium surfactants, which can have up to 26 carbon atoms include: alkoxylate quaternary ammonium (AQA) surfactants as discussed in U.S. Pat. No. 6,136,769; dimethyl hydroxyethyl quaternary ammonium as discussed in U.S. Pat. No. 6,004,922; polyamine cationic surfactants as discussed in WO 98/35002, WO 98/35003, WO 98/35004, WO 98/35005, and WO 98/35006; cationic ester surfactants as discussed in U.S. Pat. Nos. 4,228,042, 4,239,660 4,260, 529 and 6,022,844; and amino surfactants as discussed in U.S. Pat. No. 6,221,825 and WO 00/47708, specifically amido propyldimethyl amine (APA).

Zwitterionic Surfactants

Non-limiting examples of zwitterionic surfactants include: derivatives of secondary and tertiary amines, derivatives of heterocyclic secondary and tertiary amines, or derivatives of quaternary ammonium, quaternary phosphonium or tertiary sulfonium compounds. See U.S. Pat. No. 3,929,678 to Laughlin et al., issued Dec. 30, 1975 at column 19, line 38 through column 22, line 48, for examples of zwitterionic surfactants; betaine, including alkyl dimethyl betaine and cocodimethyl amidopropyl betaine, $C_8$ to $C_{18}$ ($C_{12}$ to $C_{18}$) amine oxides and sulfo and hydroxy betaines, such as N-alkyl-N,N-dimethylammino-1-propane sulfonate where the alkyl group can be $C_8$ to $C_{18}$, $C_{10}$ to $C_{14}$.

Ampholytic Surfactants

Non-limiting examples of ampholytic surfactants include: aliphatic derivatives of secondary or tertiary amines, or aliphatic derivatives of heterocyclic secondary and tertiary amines in which the aliphatic radical can be straight- or branched-chain. One of the aliphatic substituents contains at least about 8 carbon atoms, typically from about 8 to about 18 carbon atoms, and at least one contains an anionic water-solubilizing group, e.g. carboxy, sulfonate, sulfate. See U.S. Pat. No. 3,929,678 to Laughlin et al., issued Dec. 30, 1975 at column 19, lines 18-35, for examples of ampholytic surfactants.

Semi-Polar Nonionic Surfactants

Non-limiting examples of semi-polar nonionic surfactants include: water-soluble amine oxides containing one alkyl moiety of from about 10 to about 18 carbon atoms and 2 moieties selected from the group consisting of alkyl groups and hydroxyalkyl groups containing from about 1 to about 3 carbon atoms; water-soluble phosphine oxides containing one alkyl moiety of from about 10 to about 18 carbon atoms and 2 moieties selected from the group consisting of alkyl groups and hydroxyalkyl groups containing from about 1 to about 3 carbon atoms; and water-soluble sulfoxides containing one alkyl moiety of from about 10 to about 18 carbon atoms and a moiety selected from the group consisting of alkyl and hydroxyalkyl moieties of from about 1 to about 3 carbon atoms. See WO 01/32816, U.S. Pat. Nos. 4,681,704, and 4,133,779.

Gemini Surfactants

Gemini Surfactants are compounds having at least two hydrophobic groups and at least two hydrophilic groups per molecule have been introduced. These have become known as "gemini surfactants" in the literature, e.g., Chemtech, March 1993, pp 30-33, and J. American Chemical Soc., 115, 10083-10090 (1993) and the references cited therein.

Cleaning Adjunct Materials

In general, a cleaning adjunct is any material required to transform a cleaning composition containing only the minimum essential ingredients into a cleaning composition useful for laundry, hard surface, personal care, consumer, commercial and/or industrial cleaning purposes. In certain embodiments, cleaning adjuncts are easily recognizable to those of skill in the art as being absolutely characteristic of cleaning products, especially of cleaning products intended for direct use by a consumer in a domestic environment.

The precise nature of these additional components, and levels of incorporation thereof, will depend on the physical form of the cleaning composition and the nature of the cleaning operation for which it is to be used.

The cleaning adjunct ingredients if used with bleach should have good stability therewith. Certain embodiments of cleaning compositions herein should be boron-free and/or phosphate-free as required by legislation. Levels of cleaning adjuncts are from about 0.00001% to about 99.9%, and such as from about 0.0001% to about 50% by weight of the cleaning compositions. Use levels of the overall cleaning compositions can vary widely depending on the intended application, ranging for example from a few ppm in solution to so-called "direct application" of the neat cleaning composition to the surface to be cleaned.

Quite typically, cleaning compositions herein such as laundry detergents, laundry detergent additives, hard surface cleaners, synthetic and soap-based laundry bars, fabric softeners and fabric treatment liquids, solids and treatment articles of all kinds will require several adjuncts, though certain simply formulated products, such as bleach additives, may require only, for example, an oxygen bleaching agent and a surfactant as described herein. A comprehensive list of suitable laundry or cleaning adjunct materials can be found in WO 99/05242.

Common cleaning adjuncts include builders, enzymes, polymers not discussed above, bleaches, bleach activators, catalytic materials and the like excluding any materials already defined hereinabove. Other cleaning adjuncts herein can include suds boosters, suds suppressors (antifoams) and the like, diverse active ingredients or specialized materials such as dispersant polymers (e.g., from BASF Corp. or Rohm & Haas) other than those described above, color speckles, silvercare, anti-tarnish and/or anti-corrosion agents, dyes, fillers, germicides, alkalinity sources, hydrotropes, anti-oxidants, enzyme stabilizing agents, pro-perfumes, perfumes, solubilizing agents, carriers, processing aids, pigments, and, for liquid formulations, solvents, chelating agents, dye transfer inhibiting agents, dispersants, brighteners, suds suppressors, dyes, structure elasticizing agents, fabric softeners, anti-abrasion agents, hydrotropes, processing aids, and other fabric care agents, surface and skin care agents. Suitable examples of such other cleaning adjuncts and levels of use are found in U.S. Pat. Nos. 5,576,282, 6,306,812 B1 and 6,326,348 B1.

Method of Use

The present invention includes a method for cleaning a surface or fabric. Such method includes the steps of contacting a modified alkoxylated polyol compound of the present invention or an embodiment of the cleaning composition comprising the modified alkoxylated polyol compound of the present invention, in neat form or diluted in a wash liquor, with at least a portion of a surface or fabric then optionally rinsing such surface or fabric. Preferably the surface or fabric is subjected to a washing step prior to the aforementioned optional rinsing step. For purposes of the present invention, washing includes but is not limited to, scrubbing, and mechanical agitation.

As will be appreciated by one skilled in the art, the cleaning compositions of the present invention are ideally suited for use in home care (hard surface cleaning compositions), personal care and/or laundry applications. Accordingly, the present invention includes a method for cleaning a surface and/or laundering a fabric. The method comprises the steps of contacting a surface and/or fabric to be cleaned/laundered with the modified alkoxylated polyol compound or a cleaning composition comprising the modified alkoxylated polyol compound. The surface may comprise most any hard surface being found in a typical home such as hard wood, tile, ceramic, plastic, leather, metal, glass, or may consist of a cleaning surfaces in a personal care product such as hair and skin. The surface may also include dishes, glasses, and other cooking surfaces. The fabric may comprise most any fabric capable of being laundered in normal consumer use conditions.

The cleaning composition solution pH is chosen to be the most complimentary to a surface to be cleaned spanning broad range of pH, from about 5 to about 11. For personal care such as skin and hair cleaning pH of such composition preferably has a pH from about 5 to about 8 for laundry cleaning compositions pH of from about 8 to about 10. The compositions are preferably employed at concentrations of from about 200 ppm to about 10,000 ppm in solution. The water temperatures preferably range from about 5° C. to about 100° C.

For use in laundry cleaning compositions, the compositions are preferably employed at concentrations from about 200 ppm to about 10000 ppm in solution (or wash liquor). The water temperatures preferably range from about 5° C. to about 60° C. The water to fabric ratio is preferably from about 1:1 to about 20:1.

The present invention included a method for cleaning a surface or fabric. Such method includes the step of contacting a nonwoven substrate impregnated with an embodiment of the cleaning composition of the present invention, and contacting the nonwoven substrate with at least a portion of a surface and/or fabric. The method may further comprise a washing step. For purposes of the present invention, washing includes but is not limited to, scrubbing, and mechanical agitation. The method may further comprise a rinsing step.

As used herein "nonwoven substrate" can comprise any conventionally fashioned nonwoven sheet or web having suitable basis weight, caliper (thickness), absorbency and strength characteristics. Examples of suitable commercially available nonwoven substrates include those marketed under the tradename SONTARA® by DuPont and POLYWEB® by James River Corp.

As will be appreciated by one skilled in the art, the cleaning compositions of the present invention are ideally suited for use in hard surface applications. Accordingly, the present invention includes a method for cleaning hard surfaces. The method comprises the steps of contacting a hard surface to be cleaned with a hard surface solution or nonwoven substrate impregnated with an embodiment of the cleaning composition of the present invention. The method of use comprises the steps of contacting the cleaning composition with at least a portion of the nonwoven substrate, then contacting a hard surface by the hand of a user or by the use of an implement to which the nonwoven substrate attaches.

As will be appreciated by one skilled in the art, the cleaning compositions of the present invention are ideally suited for use in liquid dish cleaning compositions. The method for using a liquid dish composition of the present invention comprises the steps of contacting soiled dishes with an effective amount, typically from about 0.5 ml. to about 20 ml. (per 25 dishes being treated) of the liquid dish cleaning composition of the present invention diluted in water. Suitable examples may be seen below in Table 5.

Generally, from about 0.01 ml. to about 150 ml. of a liquid dish cleaning composition of the invention is combined with from about 2000 ml. to about 20000 ml of water in a sink having a volumetric capacity in the range of from about 1000 ml. to about 20000 ml. The soiled dishes are immersed in the sink containing the diluted compositions then obtained, where contacting the soiled surface of the dish with a cloth, sponge, or similar article cleans them. The cloth, sponge, or similar article may be immersed in the detergent composition and water mixture prior to being contacted with the dish surface, and is typically contacted with the dish surface for a period of time ranged from about 1 to about 10 seconds. The contacting of cloth, sponge, or similar article to the dish surface is preferably accompanied by a concurrent scrubbing of the dish surface.

Another method of use will comprise immersing the soiled dishes into a water bath without any liquid dish cleaning composition. A device for absorbing liquid dish cleaning composition, such as a sponge, is placed directly into a separate quantity of undiluted liquid dish cleaning composition for a period of time typically ranging from about 1 to about 5 seconds. The absorbing device, and consequently the undiluted liquid dish cleaning composition, is then contacted individually to the surface of each of the soiled dishes to remove said soiling. The absorbing device is typically contacted with each dish surface for a period of time range from about 1 to about 10 seconds. The contacting of the absorbing device to the dish surface is preferably accompanied by concurrent scrubbing.

As will be appreciated by one skilled in the art, the cleaning compositions of the present invention are also suited for use in personal cleaning care applications. Accordingly, the present invention includes a method for cleaning skin or hair. The method comprises the steps of contacting a skin / hair to be cleaned with a cleaning solution or nonwoven substrate impregnated with an embodiment of the cleaning compositions discussed herein. The method of use of the nonwoven substrate when contacting skin and hair may be by the hand of a user or by the use of an implement to which the nonwoven substrate attaches.

Other Compositions

Other compositions that comprise the compound of the present invention may be used in personal care compositions, such as contact lens solution, used as adhesives, in the vulcanization of rubbers, used in polyurethane manufacturing processes, used in dye compositions, used as an ink composition, used as a dispersant in agricultural applications, such as a dispersant in an antifungal composition, among other compositions.

Formulations

TABLE 1

Liquid Laundry Cleaning Compositions

| Ingredients | A [% by wt.] |
|---|---|
| Linear alkylbenzenesulfonate | 10-15 |
| $C_{12-15}$ alcohol ethoxy$_{(1.1-2.5)}$ sulfate | 1-5 |
| $C_{12-13}$ alcohol ethoxylate$_{(7-9)}$ | 1-5 |
| cocodimethyl amine oxide | 0.1-1 |
| fatty acid | 1-5 |
| citric acid | 1-5 |
| Polymer c[1] | 0.5-3 |
| hydroxylated castor oil (structurant) | 5-20 |
| Water, perfumes, dyes, and other trace components | ad 100 | polymer according to any one of Examples 1-3 and formula I-IV of the present application.

TABLE 2

Low Sudsing Granular Laundry Cleaning Compositions

|  | B wt % | C wt % | D wt % |
|---|---|---|---|
| $C_{11-12}$ Linear alkyl benzene sulphonate | 7 | 5.1 | 10.2 |
| $C_{12-18(tallow)}$ alkyl sulfate | 1 | 1 | 1 |
| $C_{14-15}$ alkyl ethoxylate (EO = 7) | 3.2 | 3.2 | 3.2 |
| APA[1] | 0.94 | 0.68 | 1.36 |
| silicate builder[2] | 4.05 | — | — |
| Zeolite A[3] | 16.65 | — | — |
| Carbonate[4] | 14.04 | — | — |
| Citric Acid (Anhydrous) | 2.93 | 2.93 | 2.93 |
| acrylic acid/maleic acid copolymer[5] | 0.97 | 0.97 | 0.97 |
| Polymer[6] | 1-5 | 1-5 | 1-5 |
| Percarbonate | 12.8 | 16.18 | 13.25 |
| tetraacetylethylenediamine | 3.64 | 5.92 | 3.95 |
| 1-hydroxyethyidene-1,1-diphosphonic acid | 0.18 | 0.18 | 0.18 |
| S,S-(ethylenediamine N,N'-disuccinic acid) | 0.2 | 0.2 | 0.2 |
| $MgSO_4$ | 0.42 | 0.42 | 0.42 |
| ENZYMES[7] (% particle) | 1.26 | 1.26 | 1.26 |
| MINORS (perfume, dyes, suds stabilizers) | Ad 100 | Ad 100 | Ad 100 |

[1]$C_{8-10}$ amido propyl dimethyl amine
[2]Amorphous Sodium Silicate ($SiO_2:Na_2O$; 2.0 ratio)
[3]Hydrated Sodium Aluminosilicate of formula $Na_{12}(AlO_2SiO_2)_{12} \cdot 27H_2O$ having a primary particle size in the range from 0.1 to 10 micrometers
[4]Anhydrous sodium carbonate with a particle size between 200 μm and 900 μm
[5]4:1 acrylic acid/maleic acid, average molecular weigh about 70,000 or 6:4 acrylic acid/maleic acid, average molecular weight about 10,000)
[6]polymer according to any one of Examples 1-3 or formula I-IV of the present invention
[7]one or more enzymes such as: Protease - Proteolytic enzyme, having 3.3% by weight of active enzyme, sold by NOVO Industries A/S under the tradename SAVINASE ®; Proteolytic enzyme, having 4% by weight of active enzyme, as described in WO 95/10591, sold by Genencor Int. Inc. Alcalase - Proteolytic enzyme, having 5.3% by weight of active enzyme, sold by NOVO Industries A/S Cellulase - Cellulytic enzyme, having 0.23% by weight of active enzyme, sold by NOVO Industries A/S under the tradename CAREZYME ®. Amylase - Amylolytic enzyme, having 1.6% by weight of active enzyme, sold by NOVO Industries A/S under the tradename TERMAMYL 120T ®; Amylolytic enzyme, as disclosed in PCT/US9703635. Lipase - Lipolytic enzyme, having 2.0% by weight of active enzyme, sold by NOVO Industries A/S under the tradename LIPOLASE ®; Lipolytic enzyme, having 2.0% by weight of active enzyme, sold by NOVO Industries A/S under the tradename LIPOLASE ULTRA ®. Endolase - Endoglucanase enzyme, having 1.5% by weight of active enzyme, sold by NOVO Industries A/S.

TABLE 3

Granular Laundry Cleaning Compositions

|  | E wt % | F wt % | G wt % | H wt % |
|---|---|---|---|---|
| $C_{10-12}$ linear alkyl sulphonate | 13.4-15.0 | 15.2-17.2 | 12.7 | 12.7 |
| $C_{12-14}$ alkyl ethoxylate (EO = 9) | 2.8 | 2.8 | 3.0 | 3.0 |
| Builder[1] | 18 | — | — | — |
| Sequestrant[2] | — | 17 | — | — |
| enzyme | 0.35 | 0.40 | — | — |
| Polymer[3] | 1-2 | 1-2 | 1 | 1 |
| Carboxy Methyl Cellulose | 0.2 | 0.2 | 0.5 | — |
| suds suppressor[4] | 0.01 | 0.01 | — | — |

TABLE 3-continued

Granular Laundry Cleaning Compositions

|  | E wt % | F wt % | G wt % | H wt % |
|---|---|---|---|---|
| Polyacrylate[5] | 0.80 | 0.8 |  | 0.5 |
| buffer | 4.0 | 2.0 | 6.0 | 6.0 |
| Carbonate | 11.0 | 15.0 | 8.0 | 8.0 |
| brightener | 0.08 | 0.08 | 0.03 | 0.03 |
| Sodium Sulfate | 34.83 | 32.33 | 65.09 | 65.09 |
| Water and minors | Ad 100 | Ad 100 | Ad 100 | Ad 100 |

[1]sodium tripolyphosphate
[2]Zeolite A: Hydrated Sodium Aluminosilicate of formula $Na_{12}(AlO_2SiO_2)_{12} \cdot 27H_2O$ having a primary particle size in the range from 0.1 to 10 micrometers
[3]An modified alkoxylated polyol compound according to Examples 1-3 and formula I-IV of the present application
[4]suds suppressor
[5]Mw = 4500

TABLE 4

Hard Surface Cleaning Compositions

|  | floor cleaning wipe solution I wt % | floor cleaning solution J wt % |
|---|---|---|
| $C_{11}$ alcohol ethoxylate (EO = 5) | 0.03 | 0.03 |
| Sodium $C_8$ Sulfonate | 0.01 | 0.01 |
| Propylene Glycol n-Butyl Ether | 2 | 2 |
| 2-Phenoxyethanol | 0.05 | 0.05 |
| Ethanol |  | 3 |
| Polymer[1] | 0.015 | 0.015 |
| 2-Dimethylamino-2-methyl-2-propanol (DMAMP) | 0.01 | 0.01 |
| perfume | 0.01-0.06 | 0.01-0.06 |
| Suds suppressor[2] | 0.003 | 0.003 |
| 2-methyl-4-isothaizolin-3one + chloro derivative | 0.015 | — |
| Water and minors | Ad 100 | Ad 100 |

[1]polymer according to Examples 1-3 and formula I-IV of the present application.
[2]such as Dow Corning AF Emulsion or polydimethyl siloxane

TABLE 5

Liquid Dishwashing Cleaning Composition

|  | K | L | M |
|---|---|---|---|
| $C_{12-13}$ alcohol ethoxylate sulfate EO = 0.6 | 26 | 23 | 24 |
| Amine Oxide | 5.8 | 5.8 | 5.8 |
| $C_{8-12}$ alcohol ethoxylate EO = 8 | 2 | 2 | 2 |
| Ethanol | 2 | 2 | 2 |
| Sodium cumene sulfonate | 1.80 | 1.80 | 1.80 |
| NaCl | 1.4 | 1.4 | 1.4 |
| $MgCl_2$ | 0.2 | 0.2 | 0.2 |
| Suds Booster[1] | 0.2 | 0.2 | 0.2 |
| Polymer[2] | 0.8 | 0.8 | 0.8 |
| Water & other trace components (i.e., dye, perfume, diamine, etc.) | ad 100 | ad 100 | ad 100 |

[1]as described in U.S. Pat. No. 6,645,925 B1
[2]a polymer according to Examples 1-3 and formula I-IV of the present invention.

The dimensions and values disclosed herein aer not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A process for making a compound characterized by consisting of an ethoxylated polyol compound, the polyol compound comprising at least three hydroxy moieties, at least two of the hydroxy moieties consisting of an ethoxy moiety; wherein at least one of the ethoxy moieties comprises an anionic capping unit selected from sulfate, phosphate, or carbonate, or mixtures thereof;
   wherein the process comprises the steps of (a) ethoxylating a polyol compound comprising at least three hydroxy moieties such that the average degree of ethoxylation of at least two hydroxy moieties is between about 1 and about 100, to form an ethoxylated polyol consisting of at least two ethoxy moieties;
   (b) reacting at least two of the ethoxy moieties of the ethoxylated polyol with an anionic capping unit to form an anionic ethoxylated polyol; and
   (c) substituting an anionic capping unit with an amine capping unit to form an aminated anionic ethoxylated polyol.

2. The process of claim 1 further comprising the step of quaternizing at least one of the nitrogens of the amine capping unit thereby forming a zwitterionic ethoxylated polyol.

* * * * *